United States Patent [19]
Pollet et al.

[11] 4,451,555
[45] May 29, 1984

[54] ANTIFOGGING COMPOUNDS AND THEIR USE IN SILVER HALIDE PHOTOGRAPHY

[75] Inventors: Robert J. Pollet, Vremde; Antoon L. Vandenberghe, Hove; Roger A. Spriet, Edegem, all of Belgium

[73] Assignee: AGFA-GEVAERT, N.V., Mortsel, Belgium

[21] Appl. No.: 324,805

[22] Filed: Nov. 25, 1981

[30] Foreign Application Priority Data

Dec. 9, 1980 [GB] United Kingdom ................ 8039457

[51] Int. Cl.$^3$ .............................................. G03C 1/34
[52] U.S. Cl. .................................... 430/445; 430/489; 430/611; 430/600; 430/446; 430/448; 430/449
[58] Field of Search ............... 430/611, 489, 449, 445, 430/446, 448, 600; 568/31

[56] References Cited

U.S. PATENT DOCUMENTS 3,397,987  8/1968  Luckey et al. ...................... 430/611
3,708,303  1/1973  Salesin ............................... 430/600

Primary Examiner—Won H. Louie, Jr.
Attorney, Agent, or Firm—A. W. Breiner

[57] ABSTRACT

The present invention deals with novel antifogging compounds and their use in a method of photographic reproduction comprising developing a photographic material having at least one exposed silver halide emulsion layer in the presence of a 1-phenyl-5-mercaptotetrazole compound wherein the phenyl group bears a substituent comprising at least one thioether function.

8 Claims, No Drawings

ANTIFOGGING COMPOUNDS AND THEIR USE IN SILVER HALIDE PHOTOGRAPHY

The present invention relates to novel antifogging compounds and their use in a method of photographic reproduction, more particularly to novel antifogging compounds and/or their precursors incorporated in photographic silver halide materials and/or in photographic processing compositions.

It is well known that light-sensitive silver halide materials comprising gelatin silver halide emulsion layers are subject to fogging. Fogging in general and chemical fogging in particular may be defined as the formation of a uniform deposit of silver on development which is dependent on a whole series of circumstances and factors, namely on the nature of the emulsions, on their age, on the conditions under which they have been stored, on the development conditions, etc. For particular development conditions, the fog tends to be higher when the time of storage and/or the temperature and relative humidity of the atmosphere in which the emulsions are stored are increased. Fog also increases with the degree of development and be development at elevated temperatures and at higher pH.

In order to reduce fog formation it is common practice to incorporate fog inhibitors into the photographic material or into the developer solution. For this purpose a wide variety of inorganic and organic compounds have been used or proposed (cfr. E. J. Birr, The Stabilization of Photographic Silver Halide Emulsions, the Focal Press, London-New York).

Typical well known fog inhibitors are heterocyclic mercapto compounds, in particular mercaptotetrazoles, -triazoles and -diazoles as illustrated by Kendall et al. U.S. Pat. No. 2,403,927; Kennard et al. U.S. Pat. No. 3,266,897; Research Disclosure Vol. 116, December 1973, Item 11 684; Luckey et al. U.S. Pat. No. 3,397,987; Salesin U.S. Pat. No. 3,708,303 and Shimano et al. U.S. Pat. No. 4,264,721.

However, although having a favourable antifogging effect, most of these compounds present the drawback of retarding development or depressing the sensitivity of the photographic material (cfr. Neblette's Handbook of Photography and Reprography, 7th Ed., Van Nostrand Reinhold Company, New York—1977—page 23).

It has now been found that 1-phenyl-5-mercaptotetrazoles, the phenyl group of which bears a substituent comprising at least one thioether function, have favourable antifogging properties and, very surprisingly, often even increase the speed of photographic emulsions.

According to the present invention a method of photographic reproduction is provided comprising the development of a photographic material, having at least one exposed silver halide emulsion layer, in the presence of 1-phenyl-5-mercaptotetrazoles bearing a substituent on the phenyl group comprising at least one thioether function e.g. a thioether function as comprised in the formulae: —A—S—Z, —CO—A—S—Z or —SO$_2$—A—S—Z wherein:

A represents a straight or branched-chain alkylene group of 1 to 4 carbon atoms, and Z represents alkyl including substituted alkyl, e.g. hydroxyalkyl, alkylthioalkyl.

Preferred 1-phenyl-5-mercaptotetrazoles of the present invention correspond to the following general formula:

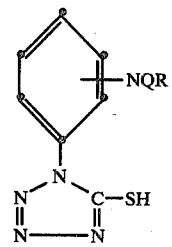

wherein:

Q represents H or lower alkyl having from 1 to 4 carbon atoms, e.g. methyl;

R represents —A—S—Z, —CO—A—S—Z or —SO$_2$—A—S—Z;

A represents a straight or branched-chain alkylene group of 1 to 4 carbon atoms, and Z represents alkyl including substituted alkyl, e.g. hydroxyalkyl, alkylthioalkyl.

It has to be emphasized that the —NQ— bridge, linking the substituent —R to the rest of the molecule, is but a non-limiting example of such linkage and that a common chemical bond or any other type of linkage can be considered as well in order to link the R-group to the phenyl group.

The use in silver halide photography of 1-phenyl-5-mercaptotetrazoles having an acylamino substituent on the phenyl group, but no thioether function, is known from U.S. Pat. No. 3,295,976 and FR Pat. No. 1,492,132.

U.S. Pat. No. 3,295,976 relates to 1-acylaminophenyl-5-mercaptotetrazoles useful in the processing of colour film as they selectively prevent negative overdevelopment when they are included in a prehardener solution, in a hydroxylamine sulphate bath or in a negative developer solution.

FR Pat. No. 1,492,132 discloses the use of 1-acylaminophenyl-5-mercaptotetrazoles adsorbed on the surface of fogged silver halide grains to reduce fogging.

The 1-phenyl-5-mercaptotetrazole compounds for use according to the present invention may be applied, as is known to those skilled in the art, in their tautomeric thione form or in the form of mercapto-precursor compounds.

Mercapto-precursor compounds are well known in the art and are described e.g. in U.S. Pat. Nos. 2,939,789; 3,311,474; 3,888,677 and 4,009,029.

In U.S. Pat. No. 2,939,789 fog reduction in photographic silver halide emulsions proceeds with azolyl mercaptoalkane diones prepared by allowing to react a 2-mercapto-substituted azole of the imidazole, benzimidazole, oxazole, benzoxazole, selenazole, benzoselenazole, thiazole and benzothiazole series with a halogenated alkylene dicarboxylic compound in which the halogen is attached to a carbon atom adjacent to one carbonyl group and not more than one carbon atom remote from the other.

U.S. Pat. No. 3,311,474 relates to the use of antifogging agents consisting of heterocyclic compounds carrying a mercapto group substituted by an alkylcarbonyl radical, an arylcarbonyl radical, an alkylsulphonyl radical or an arylsulphonyl radical, said radicals being in their turn either or not substituted.

Other suitable mercapto-precursors are the disulphides of the compounds corresponding to the abovesaid general formulae.

The U.S. Pat. No. 3,888,677 relates to silver halide photographic material containing an antifogging agent, whose mercapto group is inactivated by substitution with a heterocyclic radical and is set free in the alkaline pH medium of the developer in order to reduce overdevelopment fog in the photographic material.

In the U.S. Pat. No. 4,009,029 particular cyanoethyl-containing blocked development restrainers are described that are also called "development-restrainer precursors". They still permit the necessary development to occur before functioning in their role as development restrainers or development arrestors. The precursors contain in their structure a heterocyclic nitrogen-containing 5- or 6-membered ring carrying a sulphur atom linked to a cyanoalkyl group that by hydrolysis of the precursor compound is separated from the remainder of the molecule leaving a heterocyclic mercapto or mercaptide compound acting an antifoggant and development restrainer.

Photographic silver halide emulsion elements containing a precursor convertible to an antifoggant are designed to provide timely release of the antifoggant, in particular when the photographic element is processed with an alkaline processing composition.

The scope of the present invention is therefore not limited to the use of the defined 1-phenyl-5-mercaptotetrazoles but it also includes the use of precursors e.g. of the types referred to hereinabove.

According to the present invention there is further provided a light-sensitive photographic material comprising at least one silver halide emulsion layer and at least one compound of the type referred to hereinabove. There is also provided a photographic processing solution, preferably a developer composition comprising at least one compound of the type referred to hereinabove.

The following typical syntheses illustrate the way of preparation of some representative compounds or precursors thereof.

COMPOUND 1

1-[m(methylthioacetylamino)-phenyl]-5-mercaptotetrazole

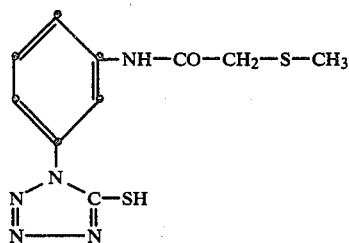

(a) A suspension of 111.5 g (0.5 mol) of 1-(m-nitrophenyl)-5-mercaptotetrazole (prepared according to the method described in BE Pat. No. 671,402), in 1 l of methanol was prepared in a 3 l stainless steel hydrogenation autoclave.

To this suspension 0.5 g of rhenium heptasulphide was added and the volume was brought up to 1150 ml with methanol.

The autoclave was then brought under a hydrogen pressure of 10 MPa and was heated to 100° C. under agitation. The autoclave was kept at this temperature until the theoretical amount of hydrogen was consumed (approximately 3 h). After cooling, the excess of hydrogen was released and the catalyst was removed by filtration. The product 1-(m-aminophenyl)-5-mercaptotetrazole was isolated by concentrating the reaction solution.

Yield: 70 g 72%).

Melting point: 205° C.; —NH$_2$ content: 96%.

(b) 48.3 g (0.25 mol) of 1-(m-aminophenyl)-5-mercaptotetrazole was dissolved under heating in 400 ml of dry dioxan and 19.75 g (0.25 mol) of pyridine. The solution was then cooled to about 20° C. and 31.25 g (0.25 mol) of methylthioacetyl chloride [A. Mooradian et al., J. Am. Chem. Soc. 71, 3372 (1949)] was added dropwise with stirring. The temperature of the mixture was allowed to rise to about 40° C.

The mixture was poured out with stirring into a vessel containing 750 ml of 1N hydrochloric acid. The precipitate was filtered off by suction, washed, dried and recrystallized from n-propanol. Yield: 47 g (67%), melting point: 198° C; —SH content: 99%.

COMPOUND 2

1-[m-(3-methylthiopropionylamino)-phenyl]-5-mercaptotetrazole

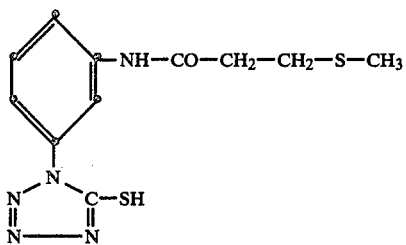

This compound was prepared from 1-(m-aminophenyl)-5-mercaptotetrazole and 3-methylthiopropionyl chloride [A. Mooradian et al., J. Am. Chem. Soc. 71, 3372 (1949)] according to the same reaction scheme as the one described hereinabove for compound 1.

Yield: 67%. Melting point: 200° C.

COMPOUND 3

1-[p-(methylthioacetylamino)-phenyl]-5-mercaptotetrazole

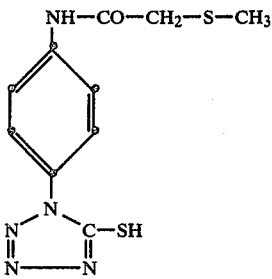

(a) 89.2 g (0.4 mol) of 1-(p-nitrophenyl)-5-mercaptotetrazole, prepared according to the method described in BE Pat. No. 671,402, was added with stirring to a solution of 270.8 g (1.2 mol) of tin(II) chloride dihydrate in 600 ml of 6N hydrochloric acid. The mixture was allowed to boil for 5 h. The hot reaction mixture was then filtered. The compound that crystallized from the filtrate was filtered off by suction and was suspended in 300 ml of concentrated hydrochloric acid. After 30 min it was again filtered off by suction.

The precipitate was again suspended in 200 ml of water and was brought with stirring to a pH of 3 with sodium hydrogen carbonate. The precipitate was filtered off by suction, washed with water and dried.

Yield: 50 g (65%) of 1-(p-aminophenyl)-5-mercaptotetrazole.

Melting point: 220° C.; —NH2 content: 95.5%.

(b) The second step in the preparation of compound 3 starting from 1-(p-aminophenyl)-5-mercaptotetrazole was analogous to step b in the preparation of compound 1.

Yield: 67%. Melting point: 190° C.

COMPOUND 4

1-[p-(3-methylthiopropionylamino)-phenyl]-5-mercaptotetrazole

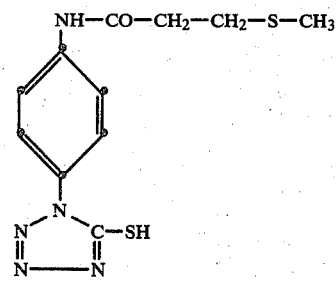

This compound was prepared from 1-(p-aminophenyl)-5-mercaptotetrazole and 3-methylthiopropyl chloride according to the synthesis described for compound 2.

Yield: 88%. Melting point: 210° C.

COMPOUND 5

1-[m-(methylthioacetylamino)-phenyl]-5-[2-(cyanoethyl)-thio]tetrazole

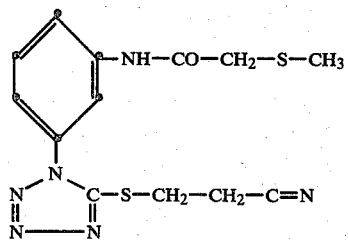

2.5 g of chloropropionitrile was added dropwise to 7 g of 1-[m-methylthioacetyl-amino)-phenyl]-5-mercaptotetrazole dissolved in 25 ml of 1N sodium hydroxide and heated at 90° C. for 16 h. The precipitate was filtered off by suction, washed with water, dried and washed with ether.

Yield: 7.5 g (90%). Melting point: 124° C.

COMPOUND 6

1-[m-(methylthioacetylamino)-phenyl]-5-[2-(ethoxycarbonyl)-thio]tetrazole

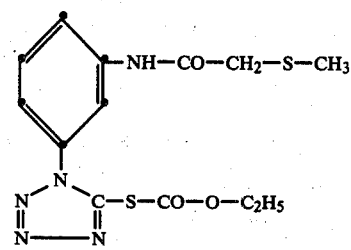

3.25 of chloroformic acid ethyl ester was added dropwise with stirring and at room temperature to 7 g of 1-[m-(methylthioacetylamino)-phenyl]-5-mercaptotetrazole dissolved in 25 ml of 1N sodium hydroxide. The precipitate was filtered off by suction and washed with ether.

Yield: 7.5 g (85%). Melting point: 128° C.

COMPOUND 7

1-[m-(methylthioacetylamino)-phenyl]-5-tetrazolyl disulphide

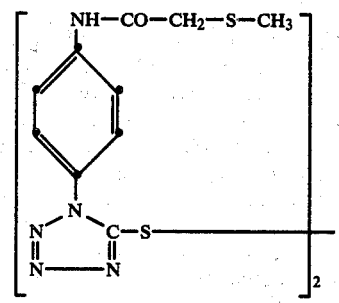

A solution of 3.0 g of potassium iodide and 3.2 g of iodine in 50 ml of water and 25 ml of ethanol was added dropwise with stirring and at room temperature to 7 g of 1-[m-(methylthioacetylamino)-phenyl]-5-mercaptotetrazole. The precipitate was purified by recrystallization from methanol.

Yield: 3 g (42%). Melting point: 145° C.

COMPOUND 8

1-[m-(2-methylthiopropionylamino)-phenyl]-5-mercaptotetrazole

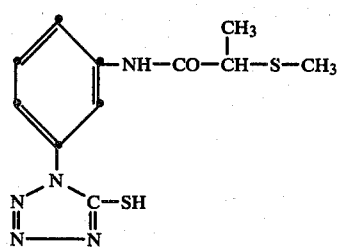

This compound was prepared according to the method described for compound 1 but starting from 1-(m-aminophenyl)-5-mercaptotetrazole and 2-(methylthio)-propionyl chloride [J. Am. Chem. Soc. 71, 3372 (1949)].

Yield: 57%. Melting point: 192° C.

In the photographic silver halide emulsions the antifoggants may be admixed with various light-sensitive silver salts, e.g. silver bromide, silver iodide, silver chloride, or mixed silver halides, e.g silver chlorobromide, silver bromoiodide, or silver chlorobromoiodide.

The silver halides can be dispersed in the common hydrophilic colloids such as gelatin, casein, zein, polyvinyl alcohol, carboxymethylcellulose, alginic acid, etc., gelatin being, however, favoured.

The amount of antifoggant for use according to the present invention may vary between wide limits and depends on each individual compound and material employed. Optimum amounts can easily be determined by routine experiments. Generally the amount varies from about 0.01 to about 5 mmol per mol of silver halide when the antifoggants are incorporated in silver halide emulsions and from about 1 to about 250 mg per liter, preferably from about 5 to about 50 mg per liter, when they are incorporated in processing liquids.

The way in which the antifoggants are added to the silver halide emulsions is not critical and the addition can take place at any stage in the emulsion preparation: they can be added before, during or after addition to the emulsion of spectral sensitizers.

They are preferably added just before coating of the emulsion on a suitable support such as e.g. paper, glass, film or metal-laminated paper.

Instead of incorporating the antifoggants into the emulsion layer, they can also be incorporated into another water-permeable colloid layer of the photographic material, e.g. a gelatin antistress layer or an intermediate layer, which is in water-permeable relationship with said emulsion layer.

The silver halide emulsions containing, in accordance with the present invention, an antifoggant, an antifoggant precursor or a mixture thereof may be chemically sensitized by effecting the ripening in the presence of small amounts of sulphur-containing compounds such as allyl thiocyanate, allyl thiourea, sodium thiosulphate, etc. The emulsions may also be chemically sensitized by means of reductors e.g. tin compounds as described in GB Pat. No. 789,823, and small amounts of noble metal compounds such as gold, platinum, palladium, iridium, ruthenium and rhodium compounds as described by R. Koslowsky, Z. Wiss. Photogr. Photophys. Photochem., 46, 65–72 (1951).

The emulsions may be spectrally sensitized or not. It is advantageous to sensitize them spectrally according to methods well known in the art to make them ortho-sensitized or panchromatically sensitized. Spectral sensitizers that can be used are, e.g., the cyanines, merocyanines, complex (trinuclear) cyanines, complex (trinuclear) merocyanines, styryl dyes, oxonol dyes and the like. Suchlike spectrally sensitizing dyes have been described by F. M. Hamer in "The Cyanine Dyes and Related Compounds" (1954).

The emulsions may be hardened in the conventional way, e.g. by means of formaldehyde, halogen-substituted aldehydes e.g. mucochloric acid and mucobromic acid, glutaraldehyde, diketones, dioxan derivatives, aziridine, oxypolysaccharides, methansulphonic acid esters, vinylsulphone compounds or hydroxydichlorotriazine.

Other conventional addenda may be added to the emulsions, e.g. plasticizers, coating aids, hardening agents, anti-staining agents, matting agents, developing agents, wetting agents, colour couplers, compounds that sensitize the emulsions by development acceleration, other fog-inhibitors and emulsion-stabilizing agents.

Compounds that sensitize the emulsions by development acceleration are, e.g., alkylene oxide polymers. These alkylene oxide polymers may be of various type, e.g. polyethylene glycol having a molecular weight of 1500 or more, alkylene oxide condensation products or polymers as described amongst others in U.S. Pat. Nos. 1,970,578—2,240,472—2,423,549—2,441,389—2,531,832 and 2,533,990; in GB Pat. Nos. 920,637—940,051—945,340—991,608 and 1,015,023 and in BE Pat. No. 648,710 or polythioethers. Other compounds that sensitize the emulsion by development acceleration and that may be used in combination with the foregoing polymeric compounds are quaternary ammonium and phosphonium compounds and ternary sulphonium compounds as well as onium derivatives of amino-N-oxides as described in GB Pat. No. 1,121,696.

The silver halide emulsions and the processing solutions may also comprise common antifoggants and emulsion stabilizers e.g. homopolar or salt-like compounds of mercury with aromatic and heterocyclic rings (e.g. mercaptotriazoles) simple mercury compounds, mercury sulphonium double salts and other mercury compounds of the kind described in BE Pat. Nos. 524,121—677,337—707,386 and 709,195, pyrimidine derivatives as described in DE-B Pat. No. 1,294,188, aminothiazole derivatives combined with derivatives of azaindenes as described in DE-B Pat. No. 1,209,426. Other suitable emulsion stabilizers are the azaindenes, particularly the tetraor pentaazaindenes and especially those substituted by hydroxyor amino groups. Suchlike compounds have been described by Birr in Z. Wiss. Photogr. Photophys. Photochem. 47, 2–58 (1952). The emulsions may further comprise as stabilizers heterocyclic nitrogen-containing mercapto compounds such as benzothiazoline-2-thione and 1-phenyl-5-mercaptotetrazole, which may comprise sulpho or carboxyl groups, mercaptocarboxylic derivatives of disulphides as described in U.S. Pat. No. 1,742,042 or derivatives of, e.g. heterocyclic mercapto compounds, nitrobenzene compounds as described in GB Pat. No. 1,399,449, disulphides, sulphinic acids such as benzenesulphinic acid and toluenesulphinic acid, thiosulphinic or thiosulphonic acids such as benzenethiosulphinic acid, toluenethiosulphonic acid, p-chloro-benzenethiosulphonic acid sodium salt, propylthiosulphonic acid potassium salt and butylthiosulphonic acid potassium salt.

According to the present invention, an exposed photographic material can also be developed in the presence of or contain more than one 1-phenyl-5-mercaptotetrazole as defined above.

Processing of photographic materials containing one or more of the above antifoggants may occur at room temperature or at elevated temperature, e.g above 30° C.

In the following examples the fog-inhibiting action of compounds corresponding to the above general formula is illustrated on samples of photographic material incorporating said compounds.

EXAMPLE 1

To several portions of a photographic ammoniacal silver bromoiodide gelatin emulsion (6 mol% of iodide)

comprising per kg an amount of silver halide equivalent to 50 g of silver nitrate, some of the antifoggants of the invention were added in a concentration of 0.35 mmol per mol of silver halide. The emulsion portions were coated on a conventional film support and dried.

The sensitometric values obtained after exposure through a step wedge of constant 0.15 and processing of a strip of the freshly prepared materials as well as the fog values for the incubated materials (5 days storage at 57° C. and 34% relative humidity) are listed in Table I.

The values given for the speed are relative values, wherein the heading "Speed I" stands for speed values measured at density (D) 0.1 above fog, whereas the values for "Speed II" derive from measurements at density 1 above fog.

The blank, i.e. the material containing no antifoggant at all, is given a speed value of 100% in such a way that the speed values of the materials containing antifoggants are percental values in respect of those of the blank. The density (D) values given for the fog are absolute values, whereas the values given for $\gamma$ are values of gradation derived from the characteristic curve over an exposure range of log E=0.60 starting from a density value of 0.5 above fog.

For the sake of comparison two additional samples are also listed in table I, said samples containing per mol of silver halide respectively 0.35 mmol of 1-phenyl-5-mercaptotetrazole, generally known as an antifoggant, and 0.35 mmol of 1-[p-acetylamino]phenyl-5-mercaptotetrazole, an antifogging agent of the type referred to in U.S. Pat. No. 3,295,976 and FR Pat. No. 1,492,132, the latter compound being structurally closely related to the compounds of the present invention.

The strips were developed at 20° C. for 5 min in a developing solution having the following composition:

| water | 800 ml |
| --- | --- |
| p-monomethylaminophenol sulphate | 1.50 g |
| anhydrous sodium sulphite | 50 g |
| hydroquinone | 6 g |
| anhydrous sodium carbonate | 32 g |
| potassium bromide | 2 g |
| water to make | 1000 ml |
| | (pH = 10.5) |

TABLE I

| Antifoggant | Fog | $\gamma$ | Speed I | Speed II | Fog (incubated material) |
| --- | --- | --- | --- | --- | --- |
| Blank | 0.20 | 1.36 | 100 | 100 | 1.16 |
| 1-phenyl-5-mercaptotetrazole | 0.14 | 1.47 | 87 | 97 | 0.20 |
| 1-[p-acetylamino]-phenyl-5-mercaptotetrazole | 0.18 | 1.46 | 90 | 103 | 0.22 |
| compound 1 | 0.10 | 1.50 | 93 | 119 | 0.20 |
| compound 2 | 0.10 | 1.45 | 119 | 119 | 0.24 |
| compound 3 | 0.14 | 1.34 | 123 | 115 | 0.22 |
| compound 4 | 0.12 | 1.35 | 107 | 115 | 0.28 |

As can be seen from the results in Table I, the compounds according to the present invention show very good sensitometric properties and, very surprisingly, their favourable antifogging action does not involve desensitization as in the case for structurally related antifoggants known so far, but on the contrary, the compounds of the invention do even enhance the speed of emulsions.

Due to the favourable sensitometric results obtained with the compounds of the present invention, the application of the latter compounds in photographic silver halide materials now allows to use a lesser amount of silver than was necessary so far for obtaining the same results.

EXAMPLE 2

An X-ray emulsion being stabilized with the curtomary amounts of 1-phenyl-5-mercaptotetrazole, 5-methyl-7-hydroxy-1,3,4-triazaindolizine and 2,3-dimethylbenzothiazolium p-tolusulphonate was divided into several portions. One of them was referred to as the blank, whereas to another one 1-[p-acetylamino]-phenyl-5-mercaptotetrazole was added in a concentration of 126 mg per mol of silver halide, for comparison purpose as the latter compound is an antifogging agent of the type referred to in U.S. Pat. No. 3,295,976 and in FR Pat. No. 1,492,132 which is structurally closely related to the compounds of the present invention.

To each of the other portions of the abovesaid X-ray emulsion one of the antifoggants of the invention was added in a concentration of 126 mg per mol of silver halide.

All of the emulsion samples were coated on a conventional support and dried. The dried samples comprised per square meter an amount of silver halide equivalent to 28 g of silver nitrate.

The sensitometric values obtained after exposure (83 kV) through a step wedge of constant 0.15 and processing of a strip of the freshly prepared materials in a developer of the type described in Example 1 at 21° C. for 7 min are listed in Table II.

The values for the speed are relative values measured at a density (D) 2 above fog and the speed of the blank is given the value of 100%.

The values for the fog and for $\gamma$ are defined as in Example 1.

TABLE II

| Antifoggant | Fog | $\gamma$ | Speed |
| --- | --- | --- | --- |
| Blank | 0.21 | 4.54 | 100 |
| 1-[p-acetylamino]-phenyl-5-mercaptotetrazole | 0.25 | 5.00 | 102 |
| compound 1 | 0.17 | 4.61 | 110 |
| compound 6 | 0.18 | 4.91 | 112 |
| compound 7 | 0.19 | 4.61 | 112 |
| compound 8 | 0.17 | 4.68 | 107 |

This example also illustrates quite clearly the remarkable decrease of fog accompanied with a surprising increase of speed when antifoggants according to the present invention are used.

The photographic material of the present invention comprises a support and at least one light-sensitive silver halide emulsion layer wherein the emulsion layer and/or a hydrophilic colloid layer in water-permeable relationship with the emulsion layer comprises an antifoggant or antifoggant precursor as defined hereinbefore.

1-Phenyl-5-mercaptotetrazoles as defined above or precursors thereof may be incorporated into various types of light-sensitive silver halide emulsions, e.g. in X-ray emulsions including both medical as well as industrial for non-destructive testing materials, graphic emulsions and emulsions intended for so-called amateur and professional photography, in continuous tone or high contrasty emulsions, in silver halide emulsions suited for silver complex or colour diffusion transfer processes, in non-spectrally sensitized emulsions and in spectrally sensitized emulsions. They may be incorporated in high-speed or low-speed black-and-white and colour emulsions.

We claim:

1. A photographic material comprising one or more hydrophilic colloid layers including at least one silver halide emulsion layer, at least one of said layers containing in an amount sufficient to inhibit fog a 1-phenyl-5-mercaptotetrazole compound or a precursor thereof, wherein the phenyl group bears a substituent comprising at least one thioether function.

2. A photographic material according to claim 1, wherein the said 1-phenyl-5-mercaptotetrazole compound corresponds to the general formula:

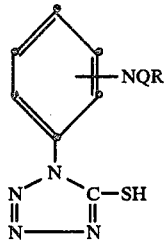

wherein:
Q represents H or lower alkyl having from 1 to 4 carbon atoms;
R represents —A—S—Z, —CO—A—S—Z or —SO$_2$—A—S—Z;
A represents a straight- or branched-chain alkylene group of 1 to 4 carbon atoms, and
Z represents an alkyl group.

3. A photographic material according to claim 1, wherein the said 1-phenyl-5-mercaptotetrazole compound or a precursor thereof, is present in a concentration of from 0.01 to 5 mmol per mol of silver halide.

4. A photographic material according to claim 1, comprising furthermore one or more compounds selected from the group consisting of
5-methyl-7-hydroxy-1,3,4-triazaindolizine,
1-phenyl-5-mercaptotetrazole and
2,3-dimethylbenzothiazolium p-tolusulphonate.

5. A photographic developer composition for use in silver halide photography comprising a silver halide developing agent and between 1 and 250 mg per liter of a 1-phenyl-5-mercaptotetrazole fog inhibiting compound or a precursor thereof, wherein the phenyl group bears a substituent comprising at least one thioether function.

6. A photographic developer composition according to claim 5, wherein the said 1-phenyl-5-mercaptotetrazole fog inhibiting compound corresponds to the general formula:

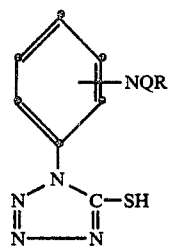

wherein:
Q represents H or lower alkyl having from 1 to 4 carbon atoms;
R represents —A—S—Z, —CO—A—S—Z or —SO$_2$—A—S—Z;
A represents a straight- or branched-chain alkylene group of 1 to 4 carbon atoms, and
Z represents an alkyl group.

7. A method of photographic reproduction comprising developing a silver halide photographic material having at least one exposed silver halide emulsion layer having present therein in an amount sufficient to inhibit fog a 1-phenyl-5-mercaptotetrazole compound or a precursor thereof, wherein the phenyl group bears a substituent comprising at least one thioether function.

8. A method according to claim 7, wherein the said 1-phenyl-5-mercaptotetrazole compound corresponds to the general formula:

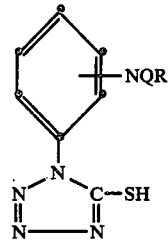

wherein:
Q represents H or lower alkyl having from 1 to 4 carbon atoms;
R represents —A—S—Z, —CO—A—S—Z or —SO$_2$—A—S—Z;
A represents a straight- or branched-chain alkylene group of 1 to 4 carbon atoms, and
Z represents an alkyl group.

* * * * *